United States Patent
Pascal et al.

(10) Patent No.: US 8,147,891 B2
(45) Date of Patent: Apr. 3, 2012

(54) USE OF AN ACARICIDAL POWDER

(75) Inventors: Jean-Philippe Pascal, Nancy (FR); Nicolas Palangie, Varese (IT)

(73) Assignee: SOLVAY (Societe Anonyme), Brussels (BE)

( * ) Notice: Subject to any disclaimer, the term of this patent is extended or adjusted under 35 U.S.C. 154(b) by 229 days.

(21) Appl. No.: 10/539,570

(22) PCT Filed: Dec. 18, 2003

(86) PCT No.: PCT/EP03/14524
§ 371 (c)(1),
(2), (4) Date: Jun. 17, 2005

(87) PCT Pub. No.: WO2004/056184
PCT Pub. Date: Jul. 8, 2004

(65) Prior Publication Data
US 2006/0040031 A1 Feb. 23, 2006

(30) Foreign Application Priority Data
Dec. 19, 2002 (FR) ...................................... 02 16448

(51) Int. Cl.
*A23L 1/36* (2006.01)
*A23L 3/34* (2006.01)
*A01N 25/08* (2006.01)
*A01N 25/34* (2006.01)
*A61K 33/00* (2006.01)
*A61K 33/02* (2006.01)

(52) U.S. Cl. ........ 426/532; 426/331; 424/409; 424/411; 424/717; 424/724; 252/8.61

(58) Field of Classification Search .................. 426/331, 426/532; 424/409, 717, 724, 411; 252/8.6
See application file for complete search history.

(56) References Cited

U.S. PATENT DOCUMENTS

| 4,599,233 | A | * | 7/1986 | Misato et al. ................. 424/717 |
| 5,342,630 | A | | 8/1994 | Jones |
| 5,439,690 | A | | 8/1995 | Knight |
| 5,576,007 | A | | 11/1996 | Ikeda et al. |
| 5,773,017 | A | | 6/1998 | Fields et al. |
| 6,887,899 | B1 | * | 5/2005 | Bessette ........................ 514/546 |
| 2002/0028256 | A1 | * | 3/2002 | Bessette ........................ 424/725 |
| 2006/0159777 | A1 | | 7/2006 | Pascal et al. |
| 2007/0037706 | A1 | | 2/2007 | Palangie et al. |
| 2008/0171069 | A1 | | 7/2008 | Pascal et al. |
| 2008/0213327 | A1 | | 9/2008 | Pascal et al. |
| 2008/0311168 | A1 | * | 12/2008 | Rochat et al. ................. 424/411 |

FOREIGN PATENT DOCUMENTS

| EP | 0 579 951 | 1/1994 |
| EP | 1 401 279 | 3/2004 |
| JP | 05/039206 | 2/1993 |
| JP | 05/201818 | 8/1993 |
| JP | 06/040806 | 2/1994 |
| WO | 02-102158 | 12/2002 |
| WO | WO 02/102158 | 12/2002 |

OTHER PUBLICATIONS

Applying Pesticides Correctly: A Guide for Private and Commercial Applicators. 1992. The Ohio State University.*
Mills, J.T. Insect-Fungus Associations Influencing Seed Deterioration. Phytopathology. 1983. vol. 73 (2). pp. 330-335.*
Montville, T.J., Goldstein, P.K. 1989. "Sodium Bicarbonate Inhibition of Aflatoxigenesis in Corn." J. Food Protect. vol. 52 (1). pp. 45-48.*
NPL "Industrial Minerals and their uses: a handbook and formulary" edited by Peter A. Ciullo , pp. 444,452.1996. Noyes Publication 369, Fairview Ave. Westwood, New Jersey, 07675.*
NPL: "acarid killer", http://www.grocerydirect.com , May 2002 (Retrieved from waybackmachine).*
U.S. Appl. No. 11/908,683, filed Sep. 14, 2007, Pascal et al.
U.S. Appl. No. 11/908,504, filed Sep. 13, 2007, Pascal et al.
U.S. Appl. No. 13/232,072, filed Sep. 14, 2011, Pascal, et al.

* cited by examiner

*Primary Examiner* — Humera Sheikh
*Assistant Examiner* — Bhaskar Mukhopadhyay
(74) *Attorney, Agent, or Firm* — Oblon, Spivak, McClelland, Maier & Neustadt, L.L.P.

(57) ABSTRACT

Use of a powder comprising more than 40% by weight of sodium bicarbonate, for its acaricidal effects in the storage of cereals.

13 Claims, No Drawings

USE OF AN ACARICIDAL POWDER

The invention relates to the use of an acaricidal powder. More particularly, it relates to its use for protecting cereals.

The term "acaricidal powder" is intended to mean a powder in contact with which acarids cannot survive. The acarids can be in egg form, larval form or adult form. The action of the powder can be direct. It can also be indirect, for example when the acaricidal powder destroys a substance that is required for survival of the acarid.

Acarids are small arachnids, close to a tenth of a millimetre in size, that develop in particular in bedding and carpeting in homes and that are capable of causing allergic reactions in humans. Their optimal living conditions require a humidity of between 55 and 85% and a temperature of between 15 and 35° C. Acarids feed essentially on the squamae and organic substances that accumulate in thick textiles. A human adult loses on average 1.5 g of dead skin a day, which is sufficient to feed 1.5 million acarids.

Among the diversity of existing acarids, some are particularly preoccupying since they develop in the human environment. These are mainly dust mites (*Dermatophagoides pteronyssinis*) and mites that develop in cereals (*Acarus siro* and *Tyrophagus putrescentiae*).

It is known and widespread practice to combat acarids by means of pyrethrum and synthetic pyrethrinoids, such as permethrin. These substances are neurotoxic and their harmfulness to humans is being increasingly established. Their use for protecting foodstuffs, and more particularly cereals, is to be avoided.

Pyrethrinoid substitutes, which are not harmful to humans and are effective in combating acarids that develop in cereal stocks are therefore demanded by many users.

The invention is directed towards providing a method that is natural and harmless to humans and that makes it possible to simply, effectively and economically eliminate the acarids that develop in cereal stocks.

Consequently, the invention relates to the use of a powder comprising more than 40% by weight of sodium bicarbonate, for its acaricidal effects in the storage of cereals.

Sodium bicarbonate is a product that is reputed to be harmless to humans. It is even authorized by various bodies (such as the FDA in the United States) in human food. Sodium bicarbonate can therefore be used without danger, in the protection of cereals, for its acaricidal effects. In addition, it has been found to be particularly effective against the acarids mentioned above that develop in cereals.

It has been observed that the acarids do not eat the acaricidal powder in accordance with the invention, but that the fine grains of this powder adhere to the outer surface of the acarids. Without wishing to be bound by a theoretical explanation and without excluding other modes of action, the inventor thinks that the use of a powder in accordance with the invention as an acaricide would damage certain membrane exchange equilibria of the cuticle of the acarid and of the shell of the egg, which would induce dehydration and in the end death thereof.

The acaricidal powder according to the invention can be used as a mixture with cereals. It can also be applied only to the walls of the means of storing (silos, bags, lorries, etc.) the cereals. The term "storage" is intended to mean, in the broad sense, not only keeping the cereal for long periods, but also keeping it for short periods that may occur during handling of harvested cereals.

In an advantageous embodiment of the invention, the cereals are stored in a silo and the powder is projected onto the walls of the silo. In this embodiment, it may, in certain cases, be preferable to apply the powder in the form of an aqueous solution or suspension and to wait for it to evaporate before introducing the cereals into the silo. After evaporation, it has been observed that the wall of the silo is covered with a very fine powder.

Powders having fine particle sizes have appeared to have a higher acaricidal capacity.

In an advantageous embodiment of the invention, a powder in which at least 90% of the granules that constitute it have a diameter of less than 500 μm is used. It is, however, preferable for the granules not to be too fine. Powders such that at least 90% of the granules that constitute them have a diameter of between 1 μm and 500 μm are generally suitable.

Acaricidal powders in accordance with the invention in which 90% of the granules have a diameter of less than 100 μm are preferred.

The acaricidal powder comprises more than 40% by weight of sodium bicarbonate. It is preferred for it to comprise at least 50% of sodium bicarbonate.

In an advantageous embodiment of the invention, the acaricidal powder comprises at least 95% of sodium bicarbonate. It may consist essentially of sodium bicarbonate.

In an advantageous embodiment of the invention, the acaricidal powder comprises no neurotoxic substance. In particular, the powder contains neither pyrethrum nor synthetic pyrethrinoids, such as permethrin.

Another aspect of the invention concerns the use of a powder according to the invention, for its combined acaricidal and insecticidal effects.

This is because cereals may also be damaged by certain insects that commonly develop therein. These are in particular the wheat weevil (*Sitophilus granarius*) and the lesser grain borer (*Rhizopertha dominica*). These insects are particularly harmful since they lay their eggs inside the cereal grains. The powder according to the invention has also appeared to combat these insects. Without wishing to be bound by a theoretical explanation and without excluding other modes of action, the inventor thinks that the mode of action of the powder according to the invention on insects differs with respect to that on acarids. This is because insects appear to absorb the sodium bicarbonate. After absorption, the bicarbonate is thought to cause an increase in pressure inside the insect through the release of gas, which is thought to cause its death.

In an advantageous embodiment of this aspect of the invention, a powder also comprising at least 1% by weight of silica is used. Silica is known for its insecticidal effects in cereals. However, it has been observed, surprisingly, that the addition of minimal amounts (for example a few percent) of silica to the bicarbonate leaves a powder whose insecticidal effects, against lesser grain borers and wheat weevils, can be greater than both those of bicarbonate alone and those of silica alone. In addition, such mixtures are of great economical advantage, sodium bicarbonate being cheaper than silica.

The silica may be amorphous or crystalline. Amorphous silica is, however, preferable since it is better tolerated by the human organism. Synthetic amorphous silicas in the form of precipitated silica are well known. The drying of precipitated silicas by atomization produces extremely fine products that are very suitable. Very good results have also been obtained with silica gels. Silica gel is the result of reacting an acid with a solution of sodium silicate. The gel obtained is then dried and finely ground. Such products have the advantage of being more economical.

In a preferred variant of this embodiment, the silica is in the form of silica gel.

The cereal stocks are also subject to damage caused by various microorganisms such as *Aspergillus* and *Penicillium*. The acaricidal powder according to the invention has also been found to be effective as a fungicide for combating these microorganisms.

Consequently, the invention also relates to the use of a powder according to the invention, for its combined acaricidal, insecticidal and fungicidal effects.

The examples for which the description follows will demonstrate the advantage of the invention.

EXAMPLE 1

10 g of sodium bicarbonate powder having a particle size such that 100% of the particles have a diameter of less than 160µ, and at least 95% have a diameter of less than 100µ, were placed at the bottom of a Petri dish. 50 "*Acarus siro*" wheat mites were then placed on the powder.

The death of 95% of the acarids (mean of 3 samples) was observed after 48 hours. In the case of a control sample, kept under the same conditions but without sodium bicarbonate, only 2% of the acarids died (mean of 3 samples).

EXAMPLE 2

The procedure was carried out as for Example 1, except that "*Tyrophagus putrescentiae*" cheese mites were used. In this case, the death of 100% of the acarids was observed after 24 hours. No acarid in the control sample was dead after 24 hours and 4% were dead after 48 hours.

Examples 1 and 2 illustrate the acaricidal effect according to the invention, in particular for acarids that develop in cereals.

EXAMPLE 3

In this example, a powder comprising 96% of sodium bicarbonate and 4% of amorphous precipitated fumed silica (Aerosil® 200 produced by Degussa) was used. The powder has a particle size such that 100% of the particles have a diameter of less than 160µ and at least 95% have a diameter of less than 100µ.

10 g of powder were placed at the bottom of a Petri dish. 50 "lesser grain borer" insects (*Rhizopertha dominica*) were then placed on the powder, along with sufficient food to ensure survival for 15 days.

The death of 47% of the insects (mean of 3 samples) was observed after 48 hours. In the case of a control sample, kept under the same conditions but without sodium bicarbonate, no insect had died (mean of 3 samples). After 72 hours, the mortality of the insects treated in accordance with the invention reaches 79% and, after 4 days, 100%, whereas that of the insects of the control sample is zero up to 72 hours and does not exceed 2% after 4 days.

EXAMPLES 4 and 5

In Examples 4 and 5, the procedure was carried out as in Example 3, except that, in Example 4, a powder consisting essentially of sodium bicarbonate was used and, in Example 5, a powder consisting essentially of silica (silica gel) was used. The mortalities after 48 hours were 2% for the bicarbonate and 100% for the silica. Comparison of Examples 3, 4 and 5 illustrates the surprising insecticidal effect obtained on the lesser grain borers by adding a minimal amount of silica to the bicarbonate powder.

Table 1 summarizes the results of the trials carried out on the lesser grain borers.

TABLE 1

Trials on *Rhizopertha dominica* (as % mortality)

|  | 48 h | 72 h | 4 days | 7 days | 10 days | 15 days |
|---|---|---|---|---|---|---|
| Sodium bicarbonate | 2% | 8% | 15% | 21% | 43% | 91% |
| Silica (silica gel) | 100% | 100% | 100% | 100% | 100% | 100% |
| Bicarb + 4% Aerosil 200 | 47% | 79% | 100% | 100% | 100% | 100% |
| Control | 0% | 0% | 2% | 5% | 9% | 11% |

EXAMPLES 6 to 8

In Examples 6 to 8, the procedure was carried out as in Examples 3 to 5, except that the lesser grain borer was replaced with the wheat weevil (*Sitophilus granarius*). The effect of various silicas and of a mixture of diatomaceous earth supplemented with 10% of silica gel was also compared. Table 2 summarizes the results obtained. They again illustrate the surprising effectiveness of the bicarbonate-silica mixtures compared with silica or bicarbonate alone. They also show the very good results obtained using silica gel.

TABLE 2

Trial on *Sitophilus granarius* (as % mortality)

|  | 24 h | 48 h | 72 h | 4 days | 7 days | 10 days | 15 days |
|---|---|---|---|---|---|---|---|
| Sodium bicarbonate | 0% | 0% | 1% | 5% | 9% | 55% | 100% |
| Diatomaceous earth + 10% silica gel | 2% | 35% | 83% | 100% | 100% | 100% | 100% |
| Bicarb + 4% Aerosil 200 | 12% | 37% | 82% | 100% | 100% | 100% | 100% |
| Bicarb + 10% silica gel | 16% | 41% | 76% | 100% | 100% | 100% | 100% |
| Bicarb + 4% Sipernat 22S | 19% | 38% | 77% | 100% | 100% | 100% | 100% |
| Control | 0% | 0% | 0% | 3% | 9% | 13% | 15% |

The invention claimed is:

1. A process for combating acarids in the storage of cereals, consisting essentially of placing the cereals in contact with a powder that consists essentially of more than 40% by weight of sodium bicarbonate and at least 4% by weight of silica wherein said cereals are infested with *Rhizopertha dominica* and wherein the powder has an insecticidal effect on the cereal such that the powder when in direct contact with the *Rhizopertha dominica* induces at least 47% of death of the *Rhizopertha dominica* after 48 hours.

2. The process according to claim 1, wherein the cereals are stored in a silo and the powder is projected onto the walls of the silo.

3. The process according to claim 1, wherein at least 90% of the granules that constitute the powder have a diameter of less than 500 µm.

4. The process according to claim 3, wherein the diameter is less than 100 µm.

5. The process according to claim 1, wherein the powder consists essentially of at least 95% by weight of sodium bicarbonate; and at least 4% by weight of silica.

6. The process according to claim 1, wherein the powder has a combined acaricidal and insecticidal effect on the cereal.

7. The process according to claim 1, wherein the silica is silica gel.

8. The process according to claim 1, wherein the powder has a combined acaricidal, fungicidal and insecticidal effect on the cereal.

9. A process for combating acarids in the storage of cereals, consisting essentially of placing the cereals in contact with a powder that consists essentially of more than 40% by weight of sodium bicarbonate, wherein said cereals are infested with *Acarus siro* and wherein the powder has an acaricidal effect on the cereal such that the powder when in direct contact with the *Acarus siro* induces at least 95% of death of the *Acarus siro* after 48 hours; or wherein said cereals are infested with *Tyrophaqus putrescientia* and wherein the powder has an acaricidal effect on the cereal such that the powder when in direct contact with the *Tyrophaqus putrescientia* induces at least 100% of death of the *Tyrophaqus putrescientia* after 24 hours.

10. The process according to claim 1, wherein the powder when in direct contact with the acarids induces at least 95% of death of acarids after 10 days.

11. The process of claim 1, wherein said cereals are infested with *Sitophilus granarius* and wherein the powder has an insecticidal effect on the cereal such that the powder when in direct contact with the *Sitophilus granarius* induces at least 10% of death of the *Sitophilus granarius* acarids after 4 days.

12. The process according to claim 9, wherein the powder consists essentially of at least 95% by weight of sodium bicarbonate.

13. The process according to claim 9, wherein the powder when in direct contact with the acarids induces at least 95% of death of acarids after 10 days.

\* \* \* \* \*